US012772995B2

(12) United States Patent
Habeych Narvaez et al.

(10) Patent No.: US 12,772,995 B2
(45) Date of Patent: Oct. 27, 2026

(54) DIAFILTRATION

(71) Applicant: COOPERATIE KONINKLIJKE AVEBE U.A., Veendam (NL)

(72) Inventors: David Ignacio Habeych Narvaez, Groningen (NL); Libbe Foekes Tjalma, Marwijksoord (NL); Robin Eric Jacobus Spelbrink, Scharmer (NL); Marc Christiaan Laus, Haren (NL)

(73) Assignee: COOPERATIE KONINKLIJKE AVEBE U.A., Veendam (NL)

( * ) Notice: Subject to any disclaimer, the term of this patent is extended or adjusted under 35 U.S.C. 154(b) by 987 days.

(21) Appl. No.: 17/613,330

(22) PCT Filed: May 25, 2020

(86) PCT No.: PCT/NL2020/050336
§ 371 (c)(1),
(2) Date: Nov. 22, 2021

(87) PCT Pub. No.: WO2020/242302
PCT Pub. Date: Dec. 3, 2020

(65) Prior Publication Data
US 2022/0240538 A1 Aug. 4, 2022

(30) Foreign Application Priority Data
May 24, 2019 (NL) ..................................... 2023197

(51) Int. Cl.
*A23J 1/00* (2006.01)
*A23J 3/14* (2006.01)
(Continued)

(52) U.S. Cl.
CPC ................. *A23J 1/006* (2013.01); *A23J 3/14* (2013.01); *B01D 61/145* (2013.01);
(Continued)

(58) Field of Classification Search
CPC ....................................................... A23J 1/006
See application file for complete search history.

(56) References Cited

U.S. PATENT DOCUMENTS

2003/0092151 A1 5/2003 Ausich et al.
2005/0208198 A1 9/2005 Kossler et al.
(Continued)

FOREIGN PATENT DOCUMENTS

CN 101367863 A 2/2009
CN 108882725 A 11/2018
(Continued)

OTHER PUBLICATIONS

Dabestani, Shirin, "Protein Recovery from Potato Processing Effluent Stream Using Ultrafiltration Membrane", Thesis—University of South Wales, Sydney-School of Chemical Engineering, Aug. 2017, (Year: 2017).*
(Continued)

*Primary Examiner* — Elizabeth Gwartney
(74) *Attorney, Agent, or Firm* — Daniel A. Thomson; Emerson Thomson Bennett LLC

(57) ABSTRACT

The present invention provides a method to isolate native tuber protein using a pretreatment of tuber processing water and diafiltration against a salt solution. This sequence of steps has the advantage that protein is stabilized during diafiltration, increasing process efficiency and protein quality and yield.

26 Claims, 4 Drawing Sheets

(51) Int. Cl.
*B01D 61/14* (2006.01)
*B01D 69/02* (2006.01)
*C07K 1/34* (2006.01)

(52) U.S. Cl.
CPC ......... *B01D 61/147* (2013.01); *B01D 61/149* (2022.08); *B01D 69/02* (2013.01); *C07K 1/34* (2013.01); *B01D 2311/18* (2013.01); *B01D 2311/2642* (2013.01); *B01D 2315/16* (2013.01); *B01D 2325/34* (2013.01)

(56) References Cited

U.S. PATENT DOCUMENTS

| | | | |
|---|---|---|---|
| 2012/0244272 | A1 | 9/2012 | Giuseppin et al. |
| 2019/0082714 | A1 | 3/2019 | Vorage et al. |
| 2019/0082715 | A1 | 3/2019 | Giuseppin et al. |

FOREIGN PATENT DOCUMENTS

| | | | | | |
|---|---|---|---|---|---|
| CN | 109068681 | A | | 12/2018 | |
| EP | 0503356 | A2 | | 9/1992 | |
| EP | 1920662 | | | 5/2008 | |
| WO | WO03003836 | | | 1/2003 | |
| WO | WO-03086102 | A2 | * | 10/2003 | .............. A61P 43/00 |
| WO | WO2008069649 | | | 6/2008 | |
| WO | WO2017146568 | | | 8/2017 | |
| WO | WO-2017146568 | A1 | * | 8/2017 | ................ A23J 1/16 |
| WO | WO2018082759 | | | 5/2018 | |
| WO | WO-2018183770 | A1 | * | 10/2018 | ............. A23C 11/06 |

OTHER PUBLICATIONS

XP029327918 Baier Anne; "Influence of High Isostatic Pressure on Structural and Functional Characteristics of Potato Protein", Food Research International, Elsevier; deel 77 (2015) pp. 753-761.

XP029894264 Kim Deok Han; "Modeling of Power Generation With Thermolytic Reverse Electrodialysis for Low-Grade Waste Heat Recovery", Applied Energy, Elsevier Science Publishers; deel 189 (2016) pp. 201-210.

XP001034682, Ralet M-C; Gueguen J, "Fractionation of Potato Proteins: Solubility, Thermal Coagulation and Emulsifying Properties", LWT—Food Science and Technology, Aug. 1, 2000 Academic Press, United Kingdom—ISSN 0023-6438, vol. 33, Nr:5, pp. 380-387.

XP004386240, Zwijnenberg H J; Kemperman A J B; Boerrigter M E; Lotz M; Dijksterhuis J F; Poulsen P E; Koops G-H, "Native Protein Recovery From Potato Fruit Juice By Ultrafiltration", Desalination, Sep. 10, 2002 Elsevier, Amsterdam, NL—ISSN 0011-9164, vol. 144, Nr:1-3, pp. 331-334.

* cited by examiner

DIAFILTRATION

BACKGROUND

There is increased demand for vegetarian and vegan analogues of conventional food products, due among others to the increased awareness of the environmental burden which comes with meat-derived food products. However, plant-based protein still cannot compete on various aspects with animal-derived products. One reason is that plant-based protein must often be isolated and processed, prior to being prepared into a food product.

Potato protein is widely available, because potato is processed on large scales to obtain starch as well as various potato products. Potato protein has an amino acid composition which makes it ideal for use in human food applications. The isolation of potato protein of sufficient quality is, however, a tedious process.

Potato protein is conventionally isolated from starch production side streams, which are prepared by grinding or mashing whole potato and subsequently isolating starch. The resulting effluent comprises potato protein, which can be isolated by various methods to obtain native or coagulated protein. Coagulated protein may be obtained by conventional methods, but has the drawback of lacking functionality and solubility. Native protein is therefore more desirable in many food applications.

Isolated native potato protein however often suffers from off-tastes and excessive color, which makes application in food products difficult. The best results are obtained using absorption or chromatography, such as expanded bed adsorption, membrane absorption or ion exchange chromatography, but these processes are expensive and laborious, in particular on an industrial scale, as they require an array of pretreatments, and must be operated at high concentration to arrive at an acceptable efficiency.

Other methods to isolate native protein have also been applied. Various membrane processes, such as ultrafiltration and diafiltration, have been applied in different settings. However, it remains a challenge to isolate protein with sufficient quality using (only) such methods, as protein is often not sufficiently pure. In addition, membrane processes suffer from membrane clogging, which precludes application at large scale. During diafiltration, protein tends to aggregate and precipitate, which precludes application of diafiltration in a viable commercial process.

More versatile methods to isolate protein from potato side streams would increase accessibility to potato protein, and thus allow for increased accessibility to a functionally ideal plant-based protein, thereby increasing sustainability of the food supply. The present invention provides an optimized method for native potato protein isolation, based on diafiltration, which can be executed at large scale.

DETAILED DESCRIPTION

Figure 1:
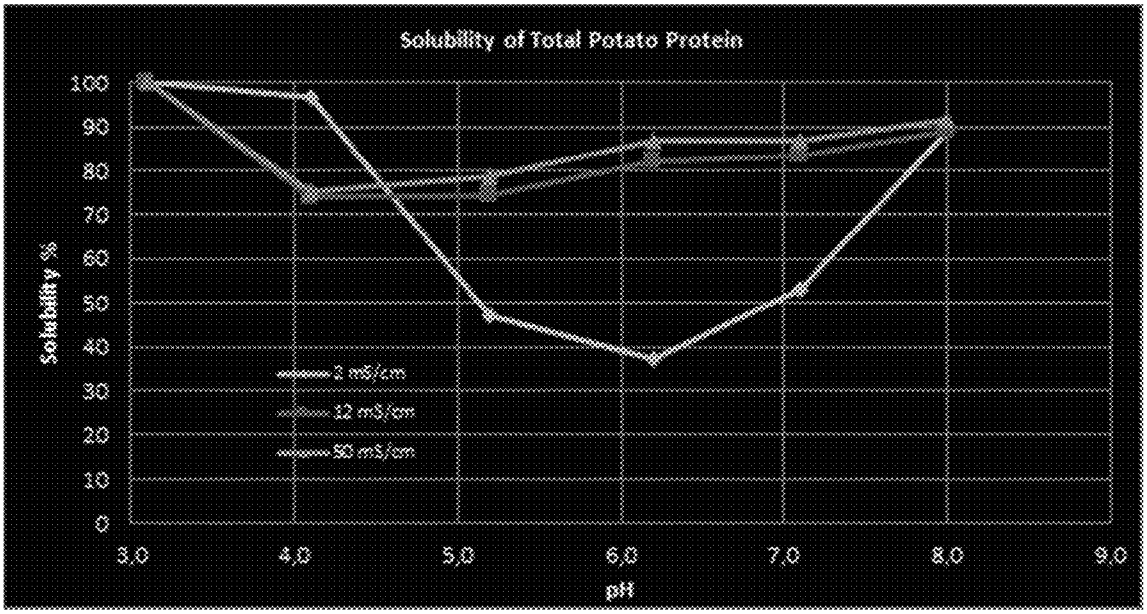
FIG. 1: solubility of potato protein at various pH and conductivities.

The invention is directed to a method for isolating a native tuber protein isolate, comprising a) processing at least one tuber to obtain tuber processing water comprising native tuber protein;
b) subjecting said tuber processing water to a pretreatment comprising one or more of the following steps:
   ba) concentration; and/or
   bb) dilution; and/or
   bc) pH adjustment; and/or
   bd) flocculation; and/or
   be) heat treatment; and/or
   bf) solids removal;
   which pretreatment results in a pretreated tuber processing water having a conductivity of 2-20 $mS\cdot cm^{-1}$, comprising native tuber protein;
c) a step of diafiltration of the pretreated tuber processing water against a salt solution having a conductivity of at least 5 $mS\cdot cm^{-1}$ using a 5-300 kDa membrane;

thereby obtaining said tuber protein isolate as the diafiltration retentate.

It is an advantage of the present method that native tuber protein can be isolated on a large scale, from various process streams. This can be achieved with high efficiency, low protein loss, low environmental burden, low cost and relatively minor waste streams, to result in a protein with high solubility, high purity and intact functional properties.

The Method

The present method is directed to the isolation of native tuber protein. A tuber in this context includes structures which may also be called root. Tuber inherently comprises protein; preferred types of tuber are also rich in starch, such as tuber types used for starch isolation.

Preferably, tuber in this context comprises potato (*Solanum tuberosum*), sweet potato (*Ipomoea batatas*), cassava (including *Manihot esculenta*, syn. *M. utilissima*, also called manioc, mandioca or yuca, and also including *M. palmata*, syn. *M. dulcis*, also called yuca dulce), yam (*Dioscorea* spp), and/or taro (*Colocasia esculenta*). More preferably, the tuber comprises potato, sweet potato, cassava or yam, even more preferably the tuber comprises potato, sweet potato or cassava, even more preferably the tuber comprises a potato or sweet potato, and most preferably the tuber comprises potato (*Solanum tuberosum*).

Preferred tuber protein comprises potato protein, sweet potato protein, cassava protein, yam protein, and/or taro protein. Potato protein is preferred. Potato is the tuber from the plant *Solanum tuberosum*, which exists in many varieties. The present method of protein isolation can be performed with any potato variety. This includes varieties intended for the starch industry (starch potatoes), as well as varieties intended for human consumption (consumption potatoes).

All tuber varieties comprise native tuber protein. Native potato protein, for example, can be divided into three classes (i) the patatin family, highly homologous acidic 43 kDa glycoproteins (40-50 wt. % of the potato proteins), (ii) basic 5-25 kDa protease inhibitors (30-40 wt. % of the potato proteins) and (iii) other proteins mostly high molecular weight proteins (10-20 wt. % of the potato proteins).

Protease inhibitor, as defined herein, is a root or tuber protein, preferably a potato protein, which in native form is capable of inhibiting the protease activity of proteases. It is common general knowledge which root or tuber protein is considered a protease inhibitor. Protease inhibitor, in the present context, refers to a root or tuber protein fraction in which at least 80 wt. %, preferably at least 85 wt. %, more preferably at least 90 wt. % of all protein has a molecular weight of at most 35 kDa as determined by SDS-page.

Patatin, as defined herein, is a root or tuber protein, preferably a potato protein, which is an acidic glycoprotein which in the tuber functions as storage protein. In the root and tuber processing industry, it is generally known which of the root or tuber proteins is considered patatin. Patatin, in the present context, refers to a root or tuber protein fraction in which at least 80 wt. %, preferably at least 85 wt. %, more preferably at least 90 wt. % of all protein has a molecular weight of more than 35 kDa as determined by SDS-page.

SDS-page (sodium dodecyl sulfate polyacrylamide gel electrophoresis) is a generally known technique for determining the molecular weight of a protein.

The present method is directed to obtaining any native tuber protein isolate. In one embodiment, the native tuber protein isolate is a native protease inhibitor isolate. In another embodiment, the native tuber protein isolate is a native patatin isolate. In these embodiments, the tuber processing water can be subjected to a step of removal of one particular potato protein prior to the diafiltration step. This may be achieved by absorption chromatography, by selective precipitation or any other method known to separate one protein fraction from another. The protein fraction which remained in solution during such processing may subsequently be subjected to the diafiltration step as herein defined.

In much preferred embodiments, the tuber protein isolate is isolate comprising native protease inhibitor and native patatin. In further much preferred embodiments, the tuber protein isolate is a total native tuber protein isolate.

A total isolate, as used herein, refers to a protein isolate comprising protease inhibitor and patatin, as well as any other protein which is present in the tuber in question. Thus, a total native tuber protein isolate can be defined as an isolate comprising all tuber protein in native form.

A protein isolate obtained with the present method is a native protein isolate. Native in the present context means that the isolation of the protein from tuber is achieved without significantly affecting the protein. Thus, native protein is not significantly degraded and is not significantly denatured. That is, the amino acid order, the three dimensional structure and the functional properties (for example solubility and/or emulsifying properties) are essentially intact, in comparison to the protein as it occurs in tuber.

The degree of native-ness of protein can be tested by a solubilization experiment. Non-native protein is considerably less soluble in water than native protein. Protein solubility can be determined by dispersing protein in water, dividing the resulting liquid into two fractions and exposing one fraction to centrifugation at 800 g for 5 minutes to create a pellet of non-dissolved material and recovering the supernatant. By measuring the protein content in the supernatant and in the untreated solution, and expressing the protein content of the supernatant as a percentage of that in the untreated solution, the solubility is determined. Convenient methods to determine the protein content are via the Sprint Rapid Protein Analyser (CEM), by measuring the absorbance at 280 nm. In the present context, protein is considered native if the solubility of the protein is at least 55%, preferably at least 65%, more preferably at least 75%, even more preferably at least 85% or even at least 90%, more preferably at least 90%, even more preferably at least 95, most preferably at least 98%.

Isolation, in the present context, means obtaining the protein either as a (clean) solution or as a protein powder. The powder can be obtained from the solution by drying the solution. Optionally, drying is preceded by a concentration step, such as by reverse osmosis, ultrafiltration or freeze concentration. Isolation in the present context means the tuber protein is maintained in solubilized form until the tuber protein isolate is dried to obtain a native tuber protein powder. Thus, isolation preferably does not comprise a step of protein precipitation, such as with alginate, resulting in a precipitated protein fraction, and a subsequent step of resolubilization of the precipitated protein, such as by dissolving the precipitated protein fraction after isolation in an aqueous solvent, to result in the native tuber protein. Protein precipitation and subsequent resolubilization may result in minor denaturation, and a precipitated and resolubilized protein is therefore not a protein isolate according to the invention.

The present invention discloses that a native tuber protein isolate can be obtained by diafiltration (DF) against a salt solution having a conductivity of at least 5 $mS \cdot cm^{-1}$. Diafiltration is a process for removing low molecular weight compounds by diluting the retentate while removing the filtrate, using diafiltration membranes, characterized by a molecular weight cutoff value (MWCO). A MWCO value of 10 kDa means that the membrane can retain from a feed solution 90% of the molecules having molecular weight of 10 kDa. The native tuber protein isolate is obtained as the diafiltration retentate. Using diafiltration, salts present in the pretreated tuber processing water can be removed, but are replaced by the salt in the salt solution.

A diafiltration membrane (DF membrane), in the present context, is a membrane as it is used during diafiltration. Preferably, the DF membrane has a MWCO of 3-500 kDa, preferably 5-300 kDa, more preferably 5-200 kDa, such as preferably 30-200 kDa, more preferably 40-120 kDa, even more preferably 50-100 kDa. In one embodiment, the MWCO can be 3-50 kDa, preferably 5-25 kDa, such as 5-15 kDa or 15-25 kDa. In another embodiment, the MWCO can be 50-200 kDa, preferably 50-150 kDa.

Preferred DF membranes are polysulphone (PS), polyethersulphone (PES), polyvinylidenefluoride (PVDF), polyacrylonitrile (PAN), regenerated cellulose and polypropylene (PP) membranes, preferably PES or PS membranes. Preferred DF membranes are anisotropic DF-membranes. A DF membrane can be implemented as tubular, spiral wound, hollow fibre, plate and frame, or as cross-rotational induced shear alter units. Much preferred DF membranes are tubular DF membranes. Each of these membranes can have an MWCO as defined above.

In preferred embodiments, the diafiltration is performed as a continuous (cross-flow) process. Operation flux can for example be between 3 and 300 $l \cdot (h \cdot m^2)^{-1}$, preferably between 5 and 200 $l \cdot (h \cdot m^2)^{-1}$, more preferably 5 and 100 $l \cdot (h \cdot m^2)^{-1}$, more preferably 6-70, $l \cdot (h \cdot m^2)^{-1}$, more preferably between 6 and 30 $l \cdot (h \cdot m^2)^{-1}$, more preferably between 7 and 30 $l \cdot (h \cdot m^2)^{-1}$, more preferably between 9 and 20 $l \cdot (h \cdot m^2)^{-1}$.

It has been found that the main protein fractions in tuber protein, and in particular in potato protein, are oppositely charged at many pH values. Patatin has a pI of 4.8-5.2, whereas protease inhibitor has a pI of from 5.8 up to 9. Even pH values optimized for solubility cannot prevent aggregation, precipitation and clogging, in particular during diafiltration. It has been found that the conductivity of a solution has great influence on protein solubility, and that low solubility can be offset by increasing conductivity. This is important in particular during diafiltration.

It has been found that for any solution comprising a native protein isolate as herein defined, it is essential that during the whole isolation process, the conductivity is relatively high. The salt solution against which the diafiltration is performed must have a conductivity of at least 5 $mS \cdot cm^{-1}$, and the feed solution must have a conductivity of 2-20 $mS \cdot cm^{-1}$.

During diafiltration, protein experiences high mechanical stress in the vicinity of the membrane. The flow pattern during diafiltration forces various protein molecules together, which leads to a forced aggregation and precipitation. Moreover, the proteins may interact with the membrane. The mechanical stress experienced by protein during diafiltration and any membrane interactions thus result in and increases membrane clogging, which hampers industrial diafiltration of protein solutions.

It has been found that a salt solution having a conductivity of at least 5 $mS \cdot cm^{-1}$ stabilizes the protein during the mechanical stress that comes with diafiltration, thereby maintaining and even increasing protein solubility under mechanical stress. This increases flux stability, increases DF operation time, and also minimises protein loss. Therefore, it is essential that the diafiltration is performed against a salt solution. This is important in order to maintain protein stability in solution during diafiltration. The term "salt solution", as used herein, is defined as a solution comprising salts which solution has a conductivity of at least 5 $mS \cdot cm^{-1}$.

It has been found that the conductivity of the salt solution must be at least 5 $mS \cdot cm^{-1}$, preferably at least 8 $mS \cdot cm^{-1}$, more preferably at least 15 $mS \cdot cm^{-1}$, in order to retain good solubility of all tuber protein during diafiltration. In order to avoid excessive salt addition during diafiltration however, the conductivity is preferably lower than 100 $mS \cdot cm^{-1}$, more preferably below 50 $mS \cdot cm^{-1}$, more preferably below 20 $mS \cdot cm^{-1}$, even more preferably below 18 $mS \cdot cm^{-1}$.

It is furthermore essential that the conductivity of the solution to be diafiltered (the diafiltration feed solution or feed) is 2-20 $mS \cdot cm^{-1}$, preferably 5-18 $mS \cdot cm^{-1}$, more preferably 8-14 $mS \cdot cm^{-1}$. This ensures that protein does not precipitate prior to diafiltration. The pH of the diafiltration feed solution is preferably lower than 4.0 or higher than 5.5, more preferably 5.5-12, even more preferably 5.5-7.0.

In further preferred embodiments, the diafiltration is performed against a salt solution having a conductivity as defined above, preferably of 5-20 $mS \cdot cm^{-1}$, preferably 5-18 $mS \cdot cm^{-1}$, more preferably 8-15 $mS \cdot cm^{-1}$, even more preferably 9-14 $mS \cdot cm^{-1}$, such as 9-11 or 10-13 $mS \cdot cm^{-1}$.

The salt solution preferably comprises a chloride salt, such as NaCl, KCl and/or $CaCl_2$), preferably NaCl or KCl. The salt solution may preferably comprise KCl. Alternatively, the salt solution may preferably comprise NaCl. Further alternatively, the salt solution comprises a mixture of NaCl and KCl.

Preferably, the salt is NaCl. In the case of NaCl, the salt concentration in the salt solution can be 0.1-5 wt. %, preferably 0.2-2 wt. %.

The skilled person can convert the required conductivities to weight-based concentrations (or molarities) in the presence or absence of other solutes based on common general knowledge. For example, the conductivity of a 0.33 wt. % NaCl solution is 5.3 mS/cm.

In much preferred embodiments, the salt solution does not comprise heavy metal salts, such as cadmium, mercury, lead or arsenic salts. In further preferred embodiments, the salt solution furthermore comprises $NH_4HCO_3$, which increases flux.

In further preferred embodiments, the salt solution may have a pH of lower than 4.0 or higher than 5.5, more preferably 5.5-12, more preferably 5.5-8.0, even more preferably 6.0-8.0, such as 5.5-7.0 or 6.0-7.0. In preferred embodiments, this pH is maintained throughout the diafiltration. In other preferred embodiments, the salt solution used for advanced diafiltration stages has a higher pH, such pH 8.0-12.0, preferably 9.0-11.0, in order to increase membrane flux further.

Diafiltration is preferably performed at dilution rate of 5:1 to 1:10, preferably, 1:1 to 1:10 (feed: salt solution), preferably in the range of 1:1 to 1:5, more preferably 1:1 to 1:4. The DF retentate may be subjected to a second, third or even further DF stage.

These conditions result in a diafiltration retentate comprising clean native tuber protein. The diafiltration retentate comprises as a percentage of dry matter at least 75 wt. %, preferably at least 80 wt. %, more preferably at least 85 wt. %, even more preferably at least 90 wt. % native tuber protein, preferably at most 1.0 wt. %, more preferably at most 0.5 wt. %, more preferably at most 0.1 wt. % of the total of glucose, fructose and sucrose, preferably at most 1.0 wt. % tuber free amino acids, more preferably at most 0.5 wt. %, more preferably at most 0.1 wt. % tuber free amino acids, preferably at most 10 mg/kg, more preferably at most 5 mg/kg sulfite, preferably at most 200 mg/kg, more preferably at most 100 mg/kg, more preferably at most 50 mg/kg, even more preferably at most 25 mg/kg glycoalkaloids, preferably at most 5 mg/kg heavy metals selected from the group consisting of cadmium, mercury, lead and arsenic, and/or preferably at most 10 wt. % chloride salts, more preferably at most 5 wt. %. Preferably, the ash content is lower than 5 wt. %, more preferably lower than 3 wt. %, more preferably lower than 1 wt. %. Further preferably, the potassium content is lower than 4 wt. %, preferably lower than 2 wt. %, more preferably lower than 1 wt. %. In much preferred embodiments, the diafiltration retentate complies with all these parameter ranges in combination. All quantities have expressed as a percentage of dry matter.

In preferred embodiments, diafiltration is performed against a salt solution throughout all diafiltration stages. In a further preferred embodiment, in particular in cases where the salt solution was applied at relatively high conductivity within the ranges herein specified, the diafiltration against a salt solution can be followed by a diafiltration stage against water at lower conductivity, or against regular water, in order to remove salts and isolate native tuber protein essentially free of salt.

Preferably, the conductivity of the solution to be diafiltered (the diafiltration feed solution or feed) remains within the ranges herein specified. Preferably in this embodiment, the pH remains the same throughout all diafiltration stages. Clogging of membranes can thus be balanced against the need for removing salt after diafiltration. In this way, a tuber protein isolate can be obtained, which has low salt contents relative to dry matter.

Alternatively, the diafiltration retentate can optionally be subjected to a step of ultrafiltration (UF). This results in concentration of the diafiltration retentate, while at the same time removing at least part of the salt which was added during the DF step. Preferably, the conductivity remains more or less constant during UF. In this way, a concentrated tuber protein isolate is obtained, which has low salt contents relative to dry matter. Preferably, the concentrated tuber protein isolate obtained from ultrafiltration complies with all parameters described above for the diafiltration retentate, but in addition has a salt content, expressed as ash, of less than 5 wt. %, preferably less than 3 wt. %, even more preferably less than 1 wt. %. Further preferably, the potassium content is lower than 4 wt. %, preferably lower than 2 wt. %, more preferably lower than 1 wt. %.

Ultrafiltration may be performed using the same or a different setup, as used for diafiltration. Thus membranes may have a MWCO of 3-500 kDa, preferably 5-300 kDa, more preferably 5-200 kDa, preferably 30-200 kDa, more preferably 40-120 kDa, even more preferably 50-100 kDa. In one embodiment, the MWCO can be 3-50 kDa, preferably 5-25 kDa, such as 5-15 kDa or 15-25 kDa, or 50-200 kDa, preferably 50-150 kDa, independent of the membrane used for diafiltration.

Preferred UF membranes are polysulphone (PS), polyethersulphone (PES), polyvinylidenefluoride (PVDF), polyacrylonitrile (PAN), regenerated cellulose and polypropylene (PP) membranes, preferably PES or PS membranes, also independent of the membrane used for diafiltration. Preferred UF membranes are anisotropic UF-membranes. A UF membrane can be implemented as tubular, spiral wound, hollow fibre, plate and frame, or as cross-rotational induced shear alter units. Much preferred UF membranes are tubular UF membranes.

Fluxes, also, may be the same or different as those obtained in diafiltration, but generally are as described above under diafiltration. UF is preferably performed so as to obtain a concentrated tuber protein isolate having a total quantity of dissolved solids of 0.5-25° Bx, preferably 5-22° Bx, more preferably 10-18° Bx, even more preferably 12-17° Bx, even more preferably 14-16° Bx. In further preferred embodiments, the total quantity of dissolved solids can be up to 30° Bx, up to 40° Bx, or up to 50° Bx.

In preferred embodiments, the same setup as used for diafiltration is also used for ultrafiltration. Thus, membranes, fluxes and other process- and equipment parameters are preferably the same. This increases process operational efficiency.

The native tuber protein isolate can subsequently be dried to obtain a native tuber protein powder. Drying can be performed by any means known in the art, preferably by spray drying or freeze drying.

Optionally, the native tuber protein isolate is subjected to a further concentration step prior to drying, preferably through reverse osmosis, evaporation or freeze concentration. How to achieve this has been described elsewhere, and is generally known.

It is much preferred that prior to drying, the tuber protein isolate is adjusted to a pH of 5.5-7.0, preferably 6.0-7.0. This increases the stability of the native tuber protein powder, which facilitates storage.

It is furthermore preferred to adjust the pH of a tuber protein isolate, in particular a concentrated aqueous tuber protein isolate, to higher than 2.5, preferably higher than 2.75. This is preferred to stabilize the viscosity of the protein solution, and avoid gelling of the solution during storage prior to drying. Preferably, such pH values are used for a tuber protein isolate comprising tuber protease inhibitor.

In addition, the pH of a concentrated tuber protein isolate can be adjusted to lower than 4.0, preferably lower than 3.5, more preferably lower than 3.0, also in order to stabilize the viscosity of the protein solution during storage prior to drying. Preferably, such pH values are used for a tuber protein isolate comprising tuber patatin.

In order to efficiently perform the present diafiltration method, it is important that a relatively clean diafiltration feed solution is used, which comprises native tuber protein as herein defined. A clean diafiltration feed solution in the present context is obtained according to steps a and b.

In step a of the present method, at least one tuber is processed to obtain an aqueous liquid comprising tuber protein. This can be called tuber processing water. This processing comprises for example pulping, mashing, rasping, grinding, pressing or cutting of the tuber, and optionally a combination with water, in order to obtain said tuber processing water comprising native tuber protein.

The aqueous liquid may comprise starch, and is preferably subjected to a step of starch removal, for example by decanting, cycloning, or filtering as is known in the art, to obtain tuber processing water comprising native tuber protein. In this embodiment, the tuber processing water is preferably a side product from the starch industry, for example potato fruit juice (PFJ) as obtained after starch isolation in the potato industry.

In other embodiments, the tuber can be processed by cutting to form shapes which are the basis for processed tuber products like for example chips and fries, preferably from potato. Such cutting, when performed in the presence of water, results in a tuber processing water comprising native tuber protein.

In one such embodiment, tuber may be processed by a water jet stream to cut the tuber. In another embodiment, tuber may be processed by cutting knives, for example in the presence of water. The water which results from such cutting processes comprises native tuber protein, and is a further preferred type of tuber processing water in the meaning of step a.

In step b, the tuber processing water is subjected at least one pretreatment step, such as concentration, dilution, pH adjustment, flocculation, solids removal and/or heat treatment, resulting in a pretreated tuber processing water comprising native protein. These steps can be performed in any order. Solids removal relates to methods to remove small insoluble particles from a solution. These insoluble particles include (aggregates of) lipids, insoluble proteins, residual cell wall fragments, small starch granules or fragments thereof, microorganisms and soil particles. The pretreatment is important in order to ensure that the tuber processing water can be efficiently processed with little if any degradation or denaturation of the protein, and to prevent clogging of filters and membranes, film- and scale-formation on the surfaces of processing equipment and to ensure high process stability and efficiency.

Concentration of the tuber processing water may be achieved by any method known in the art to remove excess water. Preferred methods are those which can be operated at relatively low temperature, such as at 40° C. or less, preferably 35° C. or less, more preferably 30° C. or less, even more preferably 25° C. or less. Further preferably, a concentration pretreatment can occur at high process speed. Preferred methods for concentrating tuber processing water are ultrafiltration, reverse osmosis and freeze concentration, preferably ultrafiltration. These methods are known in the art.

In one embodiment, concentration is achieved through freeze concentration. Freeze concentration can be performed as described in WO 2017/146568, or by other methods known in the art.

In another embodiment, concentration is achieved through reverse osmosis. Reverse osmosis can be performed using RO membranes, which do not have detectable pores as is known in the art. RO membranes separate solutes based on the different solubility of the solutes in the membrane material, as is well-known in the art. RO fluxes can be generally the same as through DF (or UF) fluxes, such as for example a flux of 2-50, preferably 5-30, more preferably 10-25 $l\cdot(h\cdot m^2)^{-1}$.

In a further, much preferred embodiment, a concentration pretreatment is achieved through ultrafiltration. Ultrafiltration has the advantage that it can be operated at high flux, while at the same time being cost efficient. Operation flux can for example be between 3 and 150 $l\cdot(h\cdot m^2)^{-1}$, preferably 5 and 50 $l\cdot(h\cdot m^2)^{-1}$, preferably between 7 and 30 $l\cdot(h\cdot m^2)^{-1}$, even more preferably between 9 and 20 $l\cdot(h\cdot m^2)^{-1}$. In preferred embodiments, the ultrafiltration is performed as a continuous (cross-flow) process.

Preferred membranes for use in an ultrafiltration pretreatment are polysulphone (PS), polyethersulphone (PES), polyvinylidenefluoride (PVDF), polyacrylonitrile (PAN), regenerated cellulose and polypropylene (PP) membranes, preferably PES and PS membranes. Preferred membranes have a molecular weight cut-off value (MWCO) of 3-500 kDa, preferably 5-300 kDa.

In case of ultrafiltration of a tuber processing water which has a relatively low quantity of suspended solids (such as juice which has low quantities of cell debris and/or which has already undergone a solids removal step), membranes preferably have a MWCO of 3-100 kDa, such as 5-50 kDa, more preferably 5-20 kDa.

In case of ultrafiltration of a tuber processing water which has a relatively high quantity of suspended solids (such as juice which has high quantities of cell debris and which has not yet undergone a solids removal step), preferred membranes have an MWCO of 20-300 kDa, preferably 50-150 kDa.

Further process conditions for an ultrafiltration pretreatment can be the same as defined above for diafiltration. In preferred embodiments, an ultrafiltration pretreatment is performed using the same setup as the diafiltration step. That is, any ultrafiltration step is preferably performed using a 5-300 kDa membrane, preferably 30-200 kDa, more preferably 40-120 kDa, even more preferably 50-100 kDa. "Any ultrafiltration step" is to be interpreted so as to express that if there is an ultrafiltration step, the ultrafiltration is preferably performed using the said membrane types. An alternative wording may be that ultrafiltration, if any, is performed using the said membrane types.

Dilution of the tuber processing water may be achieved by any method known in the art to achieve dilution. Thus, tuber processing water may be diluted with (tap or demineralized) water, a buffer or an acid or base solution. In some embodiments, dilution can be achieved through diafiltration as a pretreatment step, using the methodology and setup described above.

The pretreatment may include one or more pH adjustments. A pH adjustment may be achieved by addition of an appropriate acid or base, as is known in the art. Suitable acid or base may comprise for example hydrochloric acid, citric acid, acetic acid, formic acid, phosphoric acid, sulfuric acid, and lactic acid, and suitable bases are for example sodium or potassium hydroxide, ammonium chloride, sodium or potassium carbonate, oxides and hydroxides of calcium and magnesium.

A pH adjustment may serve various purposes. Adjustment of the pH may be used to alter the conductivity of the solution, and also influences protein solubility. In the present context, pH adjustment should not lead to full protein denaturation, as for example in acid coagulation of protein. However, adjustment of the pH of the tuber processing water may result in partial precipitation of protein, or precipitation of other constituents of tuber processing water, which may subsequently be removed by a step of solids removal.

For example, a pH adjustment to 4.0-5.5 can be used to precipitate at least part of the patatin fraction, in particular at high concentration such as at a concentration of 5-20 wt. % protein in the tuber processing water, so as to obtain tuber processing water comprising a higher relative quantity of native protease inhibitor. Precipitated protein can subsequently be removed during a step of solids removal as elsewhere defined. This increases the relative quantity of native protease inhibitor in the native tuber protein isolate.

Flocculation may be achieved by addition of an appropriate flocculant, such as for example $Ca(OH)_2$, cationic or anionic polyacrylamide, chitosan, or carrageenan. This is known in the art. The methods described in for example in WO2016/036243 may also be used. Following flocculation, a step of solids removal is preferably performed, such as by decanting, filtering, centrifugation, cycloning or microfiltration.

A heat treatment may also be applied as a pretreatment, provided that the heat treatment does not result in full protein coagulation. For example, a heat treatment to 40-55° C. for 1-120 minutes may remove a significant portion of the patatin, which can subsequently be removed by a solids removal step. Also, it is known that protease inhibitor from tuber has higher heat stability than patatin, and that heating may lead to partial or full denaturation of patatin. Thus, a heating step may be performed in combination with a solids removal step for example to obtain a tuber processing water enriched in native protease inhibitor. For example, a heat treatment at 60-80° C., preferably 70-73° C. can be used to precipitate at least part of the patatin fraction, which can be followed by a step of solids removal, in order to isolate native tuber protein enriched in native protease inhibitor.

Solids removal, in the present context, may be performed in addition to, and preferably subsequent to, another pretreatment step, as described above, but may also be performed as the only pretreatment step. Solids removal as defined here may also be performed at another point in the present method. Preferably however, solids removal is performed during the pretreatment. The pretreatment preferably comprises a step of solids removal.

Solids removal, in the present context, is preferably a step of filtration, centrifugation, cycloning, decanting, nanofiltration or microfiltration, most preferably microfiltration. These steps can be performed as is known in the art.

Microfiltration (MF) is a much preferred pretreatment in any of present embodiments, but in particular in embodiments where solids removal is the only pretreatment step. Microfiltration can be performed in order to achieve separation of fine particles from the liquid. Microfiltration can be carried out with various membranes such as polysulphones, polyvinylidenefluoride (PVDF), polyacrylonitrile (PAN) and polypropylene (PP), as well as with ceramic membranes such as zirconium or titanium or aluminum oxide membranes. MF is preferably performed over membranes having a pore size of 0.1-10 μm, preferably 0.2-4 μm, more preferably 0.3-1.5 μm.

MF can be operated either at constant pressure or at constant flow. The pressure can vary between 1.5 bar up to 5 bar. Flux may be between 0 and 350 $l\cdot(h\cdot m^2)^{-1}$, preferably between 45 and 350 $l\cdot(h\cdot m^2)^{-1}$. Microfiltration results in tuber processing water having an absorbance at 620 nm of the microfiltered liquid preferably becomes lower 0.2, more preferably lower than 0.1, against a demiwater blank.

In much preferred embodiments, the pretreatment comprises a microfiltration step. In other much preferred embodiments, the pretreatment comprises an ultrafiltration step. In a much preferred embodiment, the pretreatment comprises only, or consists of, microfiltration. In a further much preferred embodiment, the pretreatment comprises, or consists of, ultrafiltration and subsequent microfiltration, or microfiltration and subsequent ultrafiltration.

The pretreatment results in a relatively clean tuber processing water, which will be the diafiltration feed solution. The pretreatment preferably results in a diafiltration feed solution which has an absorbance at 620 nm of lower than 0.2, more preferably lower than 0.1, against a demiwater blank. The pretreatment further preferably results in a diafiltration feed solution which has a conductivity and pH as defined above. The total dissolved solids of the diafiltration feed solution is preferably 2-10° Bx, more preferably 3-8° Bx, such as 4-6° Bx. The total suspended solids less than 0.05 vol. %, preferably less 0.25 vol. %, more preferably less than 0.01 vol. %. Most preferably, suspended solids are essentially not present. Total suspended solids, in this regard, are measured by centrifuging a sample and determining the vol. % of the sediment relative to the supernatant after centrifugation.

In further much preferred embodiments, the method comprises a step of glycoalkaloid removal, to obtain a tuber protein isolate comprising at most 200 mg/kg glycoalkaloids. Glycolalkaloids in this context are glycosylated alkaloids, defined as the total of solanine and chaconine derivatives. This quantity can also be referred to as the total glycoalkaloid content (TGA), and can be determined according to the method of Laus et al: (Laus M. C., Klip G. & Giuseppin M. L. F. (2016) Food Anal. Methods 10(4) "Improved Extraction and Sample Cleanup of Tri-glycoalkaloids α-Solanine and α-Chaconine in Non-denatured Potato Protein Isolates"). Glycoalkaloids are known to be poisonous to humans, for which reason their presence should be limited in a tuber protein isolate.

Glycoalkaloid removal is essentially known, and may be achieved by adsorption to activated carbon, hydrophobic resins or various types of clay, by chromatography, by acid extraction, by enzymatic conversion or by fermentation. Exemplary techniques are described in WO 2008/056977 and WO 2008/069651. Preferably, glycoalkaloids are removed by adsorption, such as by running a process stream comprising glycoalkaloids over a column comprising a suitable adsorbent, such as activated carbon, hydrophobic resins or various types of clay. This can be done at any point in the present method, but is preferably performed as part of the pretreatment step b, or after step c.

In further preferred embodiments, the method comprises an initial step wherein at least one tuber is peeled prior to processing. Accordingly, the method provides for the processing of peeled tubers. This has the advantage that the tuber processing water that is obtained is much more clean, and therefore requires less pretreatment prior to the present diafiltration method. In addition, peeling of tubers results in a different protein composition, so that the obtained native tuber protein is enriched in the amino acids aspartic acid and asparagine, glutamic acid and glutamine, tyrosine, proline and arginine.

In much preferred embodiments, the first of diafiltration or ultrafiltration provides a permeate comprising tuber free amino acids. Thus, the permeate of the first diafiltration or ultrafiltration step is not discarded as waste, but is separately processed to obtain tuber free amino acids. Such processing preferably comprises a step of drying, preferably by spray drying and/or freeze drying, to result in a tuber free amino acid powder. Drying can be preceded by a step of concentration, such as by ultrafiltration, reverse osmosis and/or freeze concentration prior to drying, as described elsewhere.

The present method is preferably operated on an industrial scale. Thus, the present method is preferably operated to result in at least 5 kg of protein per hour, more preferably at least 25 kg protein per hour, even more preferably at least 50 kg protein per hour, potentially up to several tons per hour. In preferred embodiments, the present process can for example be operated at rates of 10-750 $m^3$/hr, preferably 50-450 $m^3$/hr, more preferably 80-300 $m^3$/hr. Preferably therefore, the method is a method in which all steps are operated continuously (as opposed to batch-wise), such as in a "continuous feed and bleed configuration" as is known to person skilled in the art.

In embodiments where tuber processing water has a high protein concentration, such as higher than 1 wt. %, preferably higher than 1.5 wt. %, the method to process tuber processing water preferably comprises a microfiltration pretreatment, followed by diafiltration as described above.

Preferably, this method furthermore comprises a flocculation step, either before or after the microfiltration step. In further preferred embodiments, the tuber processing water is furthermore subjected to an ultrafiltration step prior to the diafiltration step. In this embodiment, the method comprises a first ultrafiltration step followed by diafiltration. In further embodiments, the diafiltration retentate may be concentrated by ultrafiltration prior to drying. The first and the second ultrafiltration steps may apply the same general process conditions as described above, but need not be identical process steps.

An optimized process for isolation of native tuber protein from tuber processing water comprising a high concentration protein comprises, or consists of, the steps, in this order, of microfiltration, flocculation and diafiltration, or the steps flocculation, microfiltration and diafiltration, or the steps flocculation, microfiltration, ultrafiltration and diafiltration, or the steps microfiltration, ultrafiltration and diafiltration. In much preferred embodiments, the sequence consists of the steps microfiltration, ultrafiltration and diafiltration. Alternatively, the sequence of steps comprises, or consists of, the steps flocculation, microfiltration, ultrafiltration, diafiltration, or the steps flocculation, ultrafiltration, and diafiltration, each of which can optionally be followed by ultrafiltration.

All recited steps can be performed in accordance with the parameters elsewhere described herein. In these embodiments, a flocculation step is preferably followed by a step of solids removal, preferably centrifugation. All embodiments are preferably supplemented with a step of glycoalkaloid removal at any point in the process. Each of these methods may comprise a step of drying, which is optionally preceded by a step of concentration, preferably by ultrafiltration.

In embodiments where tuber processing water has a low protein concentration, such as below 1.5, preferably below 1 wt. %, the method preferably comprises a pretreatment comprising ultrafiltration, followed by diafiltration as described above. Preferably, this sequence of steps is preceded by a microfiltration step. Further preferably, the diafiltration retentate is subsequently ultrafiltered. An optimized process for isolation of native tuber protein from tuber processing water comprising low concentration protein consists of the subsequent steps microfiltration, ultrafiltration, diafiltration and optionally ultrafiltration and/or drying, as herein defined, supplemented with a step of glycoalkaloid removal at any point in the process.

Optionally, the diafiltration retentate or the concentrated solution obtained from ultrafiltering the diafiltration retentate, can be subjected to a fractionation step, such as by adsorption or chromatography. These methods are known to separate native tuber protein into a protease inhibitor fraction, a patatin fraction, or a total protein fraction. Thus, such methods can be applied to further purify a total tuber protein isolate, or to obtain a protease inhibitor isolate, or a patatin isolate.

In preferred embodiments however, protein isolation is achieved without a protein absorption step. The method preferably does not comprise a step of absorbing protein to an absorbent wherein protein is adsorbed to the adsorbent with high affinity (defined as protein having higher affinity for the adsorbent than the other components of the treated liquid). The method preferably does not comprise a protein absorption-elution process or protein chromatography, such as an expanded bed adsorption (EBA) process, a membrane adsorption process, or a chromatography step.

Furthermore, the method preferably also does not comprise a denaturing step. In much preferred embodiments, the method is performed so as to keep the temperature of the tuber processing water below 40° C. during the pretreatment, the diafiltration and any other step prior to drying. This aids in achieving viscosity stability of the protein solution in time, and also avoids denaturing of the protein. In addition, the present method preferably does not comprise further denaturing steps, nor a high shear step, such as for example a microparticulation step.

Protein Isolated with the Present Method

The present method has several advantages over known methods for the isolation of a native tuber protein isolate. Protein is cleaner, less degraded and less denatured (more native), and has improved functional properties. In addition, it has no off-taste and no gritty mouthfeel.

Protein isolated with the present method is clean, native protein having a high protein content. It comprises as a percentage of dry matter at least 75 wt. % native tuber protein, preferably at least 80 wt. %, more preferably at least 85 wt. %, even more preferably at least 90 wt. % native tuber protein.

The capability of isolated protein powder to dissolve in demineralized water is a measure for the degree of denaturation; denatured protein powder cannot be dissolved in water, whereas native protein powder can be dissolved in water. Native tuber protein as isolated with the present method (and subsequently dried) can be dissolved in demineralized water essentially completely, meaning that at least 55% of the isolated protein can be redissolved in demineralized water, preferably at least 65%, more preferably at least 75%, even more preferably at least 85% or even at least 90%.

The functional properties, including solubility, compare to the properties of protein as it occurs in nature, inside tuber. In addition, the emulsifying properties are not affected.

In addition, the protein comprises at most 1.0 wt. % the total of glucose, fructose and sucrose, at most 1 wt. % tuber free amino acids, at most 10 mg/kg, preferably at most 5 mg/kg sulfite, at most 200 mg/kg, preferably at most 100 mg/kg, more preferably at most 50 mg/kg, even more preferably at most 25 mg/kg glycoalkaloids, at most 5 mg/kg heavy metals selected from the group consisting of cadmium, mercury, lead and arsenic, and at most 10% chloride salts, preferably at most 5 wt. %. Preferably, the ash content is lower than 5 wt. %, preferably lower than 3 wt. %, more preferably lower than 1 wt. %.

Low sugar content and low free amino acid content are important, because sugars such as glucose, fructose and sucrose are reducing sugars, which in reaction with free amino acids can form pyrazines, which are an important contributor to off-taste.

Preferably, the sugar content is below 1.0 wt. %, preferably below 0.5 wt. %, more preferably below 0.1 wt. %, more preferably below 0.05 wt. % relative to the dry weight of the composition. Further preferably, the isolate comprises at most 1 wt. % tuber free amino acids, more preferably at most 0.5 wt. %, even more preferably at most 0.1 wt. % free amino acids, even more preferably at most 0.05 wt. % free amino acids, relative to the dry weight of the composition.

The present method advantageously reduces the quantities of both sugars and free amino acids. Diafiltration against a salt solution furthermore provides conditions where the protein is stabilized, and thus not or barely degraded during the forced mechanical interaction during diafiltration. This minimizes the formation of further free amino acids.

The present method furthermore has the effect of minimizing the sulfite presence in the obtained tuber protein isolate. Sulfite destabilizes tuber protein solutions, but is conventionally added to tuber processing water during starch processing in order to prevent oxidation, and hence color formation, of the tuber processing water. The present method effectively removes sulfite, hence leading to an increased viscosity stability.

In preferred embodiments, the method comprises removal of salts from the tuber protein isolate, in particular salts which stem from tuber, and/or salts which have been added during the diafiltration step. This can be achieved as described above, and results in protein having a low ash content, a low content of potassium, and also low quantities of heavy metals.

For the purpose of clarity and a concise description features are described herein as part of the same or separate embodiments, however, it will be appreciated that the scope of the invention may include embodiments having combinations of all or some of the features described.

The invention will now be illustrated by the following, non-limiting examples.

EXAMPLES

Glycoalkaloids (total glycoalkaloids or TGA) were determined essentially according to the method of Laus and coworkers (Laus M. C., Klip G. & Giuseppin M. L. F. (2016) Food Anal. Methods 10(4) "Improved Extraction and Sample Cleanup of Tri-glycoalkaloids α-Solanine and α-Chaconine in Non-denatured Potato Protein Isolates").

Briefly, samples were dissolved or diluted in 5% acetic acid solution containing 20 mM of heptane sulfonic acid sodium salt (VWR 152783K) for at least 2 hours. Insoluble materials were removed by centrifugation at 9000 g at ambient temperature (Heraeus Multifuge 1 SR, rotor 75002006) and the supernatant was filtered over a GHP Acrodisc 13 mm Syringe Filter with 0.45 μm GHP Membrane directly into a 1.5 mL HPLC vial (VWR 548-0004) and capped with an aluminium ci 11 mm, rubber/butyl/TEF cap (VWR 548-0010). Samples were introduced automatically onto a SPE column (Oasis HLB prospect-2/Symbiosis cartridge 2.0×10 mm particle size 30 μm) via a Robotlon online SPE system (Separations). The glycoalkaloids were eluted onto a Hypersil ODS C18 (250 mm×4.6 mm 5 μm)

column and separated using 50% acetonitrile/phosphate buffer pH 7.6. Analytes were detected using Smartline UV detector 2520 (Knauer) and quantified on a calibration curve prepared from purified glycoalkaloids (α-solanine, Carl Roth 4192,1 and α-chaconine Carl Roth 2826,1)

Metals were determined by Inductive-Coupled Plasma Mass Spectrometry (ICP-MS) according to ISO 17294-2: 2016.

Elemental compositions were determined via X-ray fluorescence (XRF) for all elements with an atomic number above that of sodium via a Rigaku CG ED-XRF (Rigaku).

Ash was determined by incineration of the sample at 550° C. and weighing the residue.

Sugar determination was performed with a Megazyme SuFrG kit according to the manufacturer's instructions.

The quantity of total suspended solids (TSS) can be determined by determining the absorbance of a juice with a dry matter content of 4.5 wt. % at 620 nm.

The quantity of dissolved solids can be determined by measuring it in a PAL alpha handheld digital refractometer (AT 3840, Atago).

Absorbance at 620 nm is determined by diluting a sample to 5.0° Bx (corresponding to 4.5 wt % of dry matter) and centrifugation at 14.000 rpm in an Eppendorf centrifuge for 10 minutes to remove insolubles. Samples whose brix values were below 5 were centrifugated as is. Aliquots of 1 mL of the supernatant of each sample are introduced in a cuvette and placed in a BioRad SmartSpec Plus spectrophotometer. Absorbance is read in duplicate at 620 nm relative to a demiwater blank.

Conductivity can be determined by a HI 98312 conductivity meter (Hanna Nindustries, Netherlands) at room temperature, as is well-known in the art. Conductivity can also be determined by calculation, where appropriate, based on the various concentrations of solutes, as is known in the art.

Protein concentrations can be determined by Kjeldahl measurements. The nitrogen-number is then converted into a protein content by multiplying with 6.25.

True protein content was determined using CEM Sprint rapid protein analyser. This method is based on the interaction of a negatively charged dye (iTAG) with the positively charged amino acids Lysine, Arginine and Histidine present in the protein under acidic conditions. The hydrophobic nature of the dye causes the proteins to precipitate and the loss of dye adsorption at 480 nm is translated to protein content by use of a calibration curve prepared from Kjeldahl analysis that was performed on thoroughly cleaned protein preparations. Nitrogenous compounds such as single amino acids and small peptides do not precipitate with the dye solution and as a consequence do not influence the protein content measurement.

Moisture content is reported as Loss-on-drying and is determined by introducing an aluminium sample pan (VWR 611-9000) containing between 1 and 10 grams of sample in an HG83 halogen dryer (Mettler Toledo), set for 100° C. for 10 minutes.

In the experiments, the following salt solutions were frequently used during diafiltration: 0.5 wt. % NaCl (conductivity 8.2 mS/cm); 0.5 wt. % KCl (conductivity 8.2 mS/m); 0.33 wt. % NaCl (conductivity 5.3 mS/cm);

Protein Composition by Experion

The protein composition is determined using an Experion Pro260 automated electrophoresis station (Bio-Rad, USA). First the reagents were equilibrated to room temperature and briefly vortexed, after which the reagents were spinned down on a centrifuge at 10000×g for 5 minutes. After this, the gel and gel-stain solutions were prepared, the former of which did not require mixing of reagents while the latter of which was made by mixing 20 μL of the stain reagent with 520 μL of the gel reagent. Both solutions were then vortexed and spinned down in an Eppendorf cup equipped with a 0.2 μm filter at 10000×g for 5 minutes. Subsequently the sample buffer was prepared by mixing 30 μL of sample buffer with 1 μL of 6-mercaptoethanol. The samples and ladder were subsequently prepared by mixing 4 μL of sample/ladder with 2 μL of sample buffer and subsequent vortexing and centrifuging at 10000×g for 5 minutes. The sample and ladder are subsequently diluted with 84 μL of ultrapure water. The Experion chip is primed with 12 μL of gel-stain solution on the priming station by running program B3. Subsequently, 12 μL of gel-stain and gel solution are pipetted in the according chip wells. 6 μL of ladder is pipetted in the ladder well on the experion chip. Subsequently, 6 μL of each sample are loaded in sample wells 1-10. Lastly, the analysis is started by loading the experion chip to the Experion Pro260 and running the Protein 260 analysis. The electrodes are cleaned using a cleaning chip after the analysis.

Example 1

The effect of salt concentration on the tendency of protein to aggregate and precipitate was evaluated using model solutions at various pH's and conductivities. The model solution comprises purified protease inhibitor and purified patatin (obtained by chromatography and extensively dialysed).

Protein was dissolved at a total protein concentration of 1 wt. % in ratio 1:1 in mass of purified protease inhibitor and purified patatin in 30 mM potassium citrate buffer. The pH was adjusted by HCl (1 M) or NaOH (1 M) as required. Conductivities were set to 2, 12 or 50 mS·cm$^{-1}$ through the addition of potassium chloride. Samples were incubated at ambient temperature for 1 hour and centrifuged during 10 minutes at 14000 rpm in a Eppendorf centrifuge to remove precipitated protein. Supernatants were diluted 25 times in a 100 mM NaOH solution. Protein concentrations were read at 280 nm on a BioRad Smartspec Plus spectrophotometer relative to a 100 mM NaOH blank and expressed as percentage of soluble protein. The results show a strong pH-dependence of potato protein solubility as a function of pH at low conductivities, while at higher conductivities the pH effect is reduced or abolished (see FIG. 1).

Example 2

The effect of salt concentration on the tendency of protein to aggregate and precipitate under mechanical stress was evaluated using model solutions at various pH's and conductivities. The model solution comprises purified protease inhibitor and purified patatin (obtained by chromatography and extensively dialysed) at a 1:1 molar ratio.

Protein was dissolved at a total protein concentration of 2 and 6 wt. % in 10 mM citrate buffer. The buffer was diluted with NaOH or HCl solution to set the pH to 6.0 or 7.0. To the resulting solution, solid KCl was added so as to set the conductivity to 2, 5, 12 and 50 mS·cm$^{1}$. The solutions were centrifuged for 5 min at 10.000×g to remove insoluble protein, and subsequently set to a final protein concentration (calibrated on the PI fraction) of 1.5 and 4 wt. %. Protein solubility was determined on each fraction separately, and subsequently averaged to reflect natural variability in potato juice.

Figure 2:
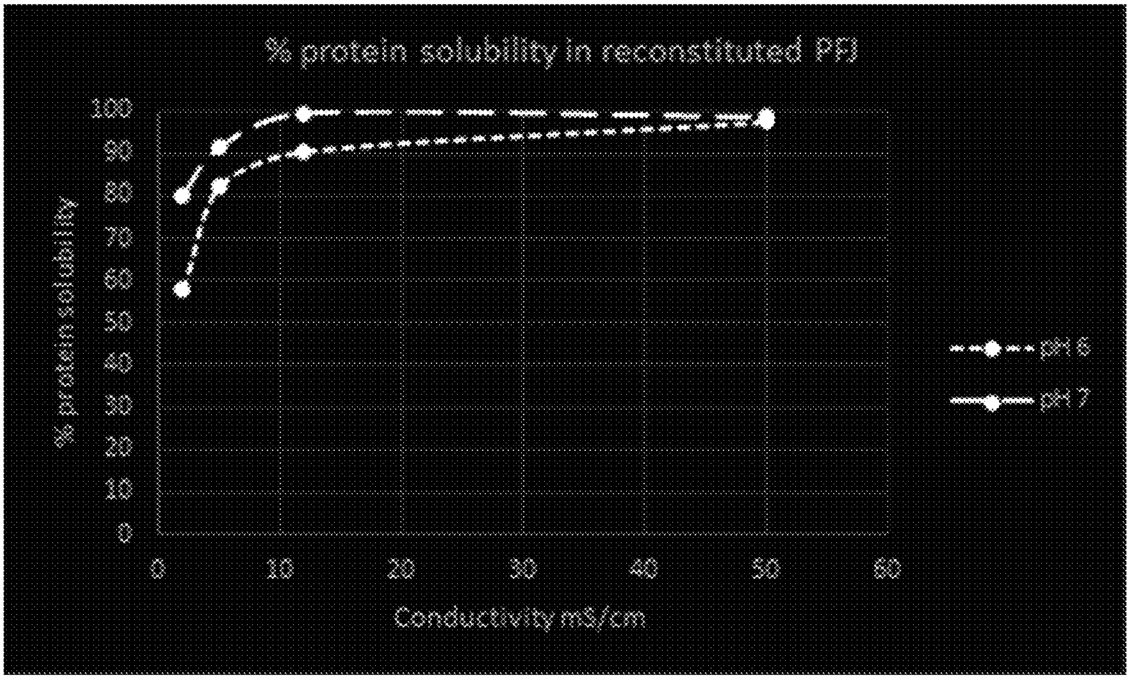
FIG. 2: solubility of potato protein at pH 6 and 7 at various conductivity, when exposed to mechanical stress.

The final protein solution was incubated for 1 hour at room temperature while stirring hard with a mechanical stirrer to mimic mechanical forces as occurring during diafiltration. The protein mixture was subsequently centrifuged for 5 min at 10.000×g and the protein concentration in de supernatant was determined. Loss of protein by aggregation was calculated by the difference between the starting protein concentration and the final protein concentration. The results are shown in FIG. 2.

The results show that total potato protein is highly soluble at increased conductivity, even under mechanical stress. The conductivity should be at least 5 mS·cm$^{-1}$, preferably at least 8 mS·cm$^{-1}$. In order to avoid excessive salt addition during diafiltration, the conductivity is preferably below 20 mS·cm$^{-1}$, more preferably below 18 mS·cm$^{-1}$. Preferred conductivities are 8-15 mS·cm$^{-1}$, preferably 9-14 mS·cm$^{-1}$.

Example 3

Tuber processing water as obtained from potato tubers after starch and fiber removal (potato processing water) was used as raw material for production of a total native protein isolate at pilot scale. Potato processing water was subjected to a solids removal pretreatment ((a) and (b)), or to a flocculation pretreatment followed by solids removal (c). In all cases, processing occurred at a flow of between 100-250 l·h$^{-1}$).

(a) The potato processing water was centrifuged in a conventional continuous stack disc centrifuge. Further removal of particles was effected using a dead-end filtration outfitted with diatomaceous earth as filter aid. The centrifuged potato processing water was stored in a tank to await further processing.

(b) The potato processing water was subjected to a step of microfiltration using ceramic membranes with a pore size of 0.8 micrometres and operated at temperature around 23±2° C. and a constant flux of 100 l·(h·m$^2$)$^{-1}$. The microfiltered potato processing water was stored in a tank to await further processing.

(c) The potato processing water was pretreated with a mixture of cationic and anionic flocculants as described in WO 2016/036243A1. The solids were separated from the potato processing water in a disc stack centrifuge. The sludge at the bottom of the centrifuge was discarded, whereas the supernatant of the centrifuge was used as feed for the diafiltration. Samples of flocculated potato processing water were taken to follow a modified sludge volume index (SVI) as indicative of flocculation quality. The supernatant was also checked for absorbance at 620 nm. The flocculated potato processing water was stored in a tank to await further processing.

Characteristics of these pretreatment steps are shown in Table 1.

TABLE 1

Characteristics of potato processing water after various pretreatments

| Flow inlet PJ (l · h$^{-1}$) | SVI (ml · g$^{-1}$) | Absorbance 620 nm |
|---|---|---|
| 100 | 49 | 0.077 |
| 150 | 64 | 0.076 |
| 200 | 63 | 0.082 |
| 250 | 71 | 0.104 |

Thus pretreated potato juice was optionally subjected to TGA removal. TGA removal was carried out in a column packed with granular activated carbon (C-GRAN, Norit). The activated carbon column was pre-soaked in demineralized water for 24 h before performing the TGA removal. The pretreated potato juice was passed over the column using 2-hour contact time.

In all cases, the pretreatment furthermore comprised an ultrafiltration step preceding the diafiltration. The potato processing water was ultrafiltrated using a spiral-wound membrane with a molecular weight cut-off (MWCO) of 5 kDa in order to obtain a concentrated potato protein solution havening a dissolved solids content between 9.9 and 21.8° Bx.

TABLE 2

Treatment and process conditions to obtain native protein isolate.

| | | Operation | | | | | | |
|---|---|---|---|---|---|---|---|---|
| | | 1 | 2 | 3 | 4 | 5 | 6 | 7 |
| | | Pre-treatment | | | | | | |
| | | MF, UF b | MF, UF b | Flocc. Centr. UF c | Centr. UF a | Flocc. Centr. UF c | Flocc. Centr. UF c | Flocc, Centr. UF c |
| MF Flux | (l · (h · m$^2$)$^{-1}$) | 100.0 | 100.0 | | | | | |
| MF TMP* | (bar) | 0.5-2.5 | 0.5-2.5 | | | | | |
| UF Flux | (l · (h · m$^2$)$^{-1}$) | 10.0 | 13.0 | 12.0 | 13.8 | 12.4 | 12.6 | 13.2 |
| T | (° C.) | 16.4 | 21.9 | 21.0 | 22.5 | 21.5 | 19.8 | 1.02-1.06 |
| UF TMP* start-end | (bar) | 1.04-1.07 | 1.04-1.06 | — | 1.05-1.07 | 1.02-1.06 | 1.02-1.05 | 15.7 |
| Solids start-end | (°Bx) | 5.9-10.8 | 5.1-15.3 | 5.6-15.2 | 5.9-10.3 | 5.5-15.3 | 5.9-10.0 | 5.3-10 |
| σ start-end | (mS · cm$^{-1}$) | 13.6-13.0 | 9.5-10.8 | 9.5-10.9 | 8.7-9.1 | 10.7-10.1 | 10.5-10.3 | 9.5-10.7 |
| Diafiltration | | | | | | | | |
| $V_{DF}$:VPJ | — | 3:1 | 4:1 | 3:1 | 3:1 | 4:1 | 3:1 | 3:1 |
| [Salt] | (%) | 0.33 | 0.33 | 0.33 | 0.33 | 0.33 | 0.66 | 0.33 |
| Flux | (l · (h · m$^2$)$^{-1}$) | 13.0 | 8.5 | 10.0 | 14.9 | 9.0 | 14.2 | 8.8 |
| TMP* start-end | (bar) | 1.05-1.12 | 1.04-1.1 | — | 1.03-1.12 | 1.04-1.09 | 1.02-1.09 | 1.02-1.05 |
| T | (° C.) | 18.5 | 20.5 | 22.0 | 24.7 | 22.7 | 22.6 | 18.5 |
| Solids start-end | (°Bx) | 10.8-15.9 | 15.3-15.7 | 15.2-16 | 10.3-19.3 | 15.3-16.8 | 10.0-16.8 | 10-9.9 |
| σ start-end | (mS · cm$^{-1}$) | 13.0-5.5 | 10.8-5.44 | 10.9-5.3 | 9.1-5.1 | 10.1-4.5 | 10.3-8.4 | 10.7-6.5 |
| TGA removal | | Yes | No | Yes | Yes | Yes | Yes | Yes |
| Drying | | Spray | Spray | Spray | Spray | Spray | Spray | Freeze |

TABLE 2-continued

Treatment and process conditions to obtain native protein isolate.

| | | Operation | | | | | | |
|---|---|---|---|---|---|---|---|---|
| | | 1 | 2 | 3 | 4 | 5 | 6 | 7 |
| | | Pre-treatment | | | | | | |
| | | MF, UF b | MF, UF b | Flocc. Centr. UF c | Centr. UF a | Flocc. Centr. UF c | Flocc. Centr. UF c | Flocc, Centr. UF c |
| Analysis | | | | | | | | |
| Kjeldahl protein | (%) | 84.8 | 80.7 | 83.7 | 81.1 | 85.5 | 82.2 | 79.0 |
| MW < 35 kDa | (%) | 58.1 | 55.0 | 77.4 | 81.6 | 66.1 | 83.2 | 54.2 |
| Moisture content | (%) | 7.73 | 6.95 | 8.43 | 9.24 | 5.51 | 7.72 | 7.62 |
| Total TGA content | (ppm) | 120 | 475 | — | 43 | 96.5 | 26 | 48 |
| Sulphite | (ppm) | <5 | <5 | <5 | <5 | <5 | <5 | 7.0 |
| Total heavy metals | (ppm) | 0.53 | 0.69 | 0.61 | 1.19 | 0.73 | 0.79 | 0.59 |

*transmembrane pressure

The retentate from the ultrafiltration was subjected to further treatment comprising diafiltration against a salt solution having 0.33 or 50.66 wt. % NaCl, at different ratios of feed to salt solution (1:3-1:4). This resulted in a potato protein isolate solution. During the ultrafiltration and diafiltration steps the pH remained at 6.3±0.3. Final concentrates were dried by spray drying (SD, $T_{in}$ 175° C., $T_{out}$ 75° C.) or by freeze drying. A summary of conditions shown in Table 2.

The potato protein isolate obtained from ultrafiltration and diafiltration against a salt solution was characterized for conductivity and concentration of dissolved solids (° Bx). The dried product has been analysed on protein content (Kjeldhal), moisture content, relative quantity of protease inhibitor, TGA content, sulphite and heavy metals.

Table 2 shows the influence of different process parameters on the quality of the protein isolate. All the different pre-treatments can be applied successfully prior to diafiltration but do not have a significant influence on the final quality of either the final concentrated aqueous protein isolate or the dried product, provided that diafiltration is performed against a salt solution. A TGA removal step is required to obtain a potato protein with the required low TGA level.

Experiment 5 shows that when the potato processing water is diafiltrated with a higher dilution factor (1:4), the conductivity of the protein isolate is lower than in the experiments where a dilution factor of 1:3 is applied. After drying, the product from experiment 5 also has the highest protein content.

When increasing the salt concentration from 0.33% to 0.66%, as was done in experiment 6, the conductivity of the protein isolate is higher. However, the TGA content of the dried protein isolate from experiment 6 is lower than is obtained with the other experiments. The table also shows that the protein isolate can be dried by various methods such as spray-drying (experiment 1-6) or freeze drying (experiment 7). In all cases a product with a high protein content from 79% up to 85.5% has been obtained.

Example 4

Tuber processing water as obtained from potato tubers after starch and fiber removal (potato processing water) was used as raw material for production of a native total potato protein isolate at pilot scale. Potato processing water was subjected to a solids removal pre-treatment step of microfiltration using ceramic membranes with a pore size of 0.8 micrometres and operated at temperature around 23±2° C. and a constant flux of 100 $l\cdot(h\cdot m^2)^{-1}$. The microfiltered potato processing water (MF-PFJ) was stored in a tank to await further processing.

In all cases the microfiltered PFJ (4.2-5.0° Bx and 12 mS/cm) was subjected to ultrafiltration using a polyethersulphone membrane with a molecular weight cut-off (MWCO) of 5 kDa or 50 kDa resulting in a retentate having a dissolved solids content between 10.5 and 28.2° Bx and conductivity ranging between 10 and 16 mS/cm.

The retentate of the ultrafiltered PFJ was subsequently subjected to TGA removal. Optionally, the retentate was diluted with soft water prior to TGA removal in order to obtain a protein solution having a dissolved solids content between 10.5 and 12.9° Bx and 6 to 13 mS/cm. TGA removal was carried out using four columns packed with hydrophobic resin at room temperature at a pH of 6-6.5. After TGA removal a protein solution is obtained having a conductivity of 8-13 mS/cm, which is optionally concentrated to a solids content ranging between 12-18° Bx.

The retentate from the ultrafiltration was subjected to further treatment comprising multiple diafiltration steps against a salt solution having 0.5 wt. % NaCl or KCl, with a conductivity of 8.2 mS/cm at different ratios of feed ($V_{PJ}$) to salt solution ($V_{DF}$)) (1:1-1:2). This resulted in a potato protein isolate solution. Final concentrates were optionally dried by spray drying (SD, $T_{in}$ 175° C., $T_{out}$ 75° C.). Each diafiltration step entails dilution of protein solution volume $V_{PJ}$ with diafiltration volume $V_{DF}$ in a ratio as indicated and concentrating the diluted protein solution back to the original volume by ultrafiltration. An overview of the conditions is shown in Table 3.

The potato protein isolate obtained from ultrafiltration and diafiltration against the salt solution was characterized for concentration of dissolved solids (° Bx). The final product has been analysed on protein content, moisture content, relative quantity of protease inhibitor. TGA content, sulphite and heavy metals.

Table 3 shows the influence of different process parameters on the quality of the protein isolate. All different pre-treatments can be applied successfully prior to diafiltration. Furthermore, different diafiltration conditions were tested, showing that a protein isolate of good quality can be obtained using different salt solutions.

Figure 6:
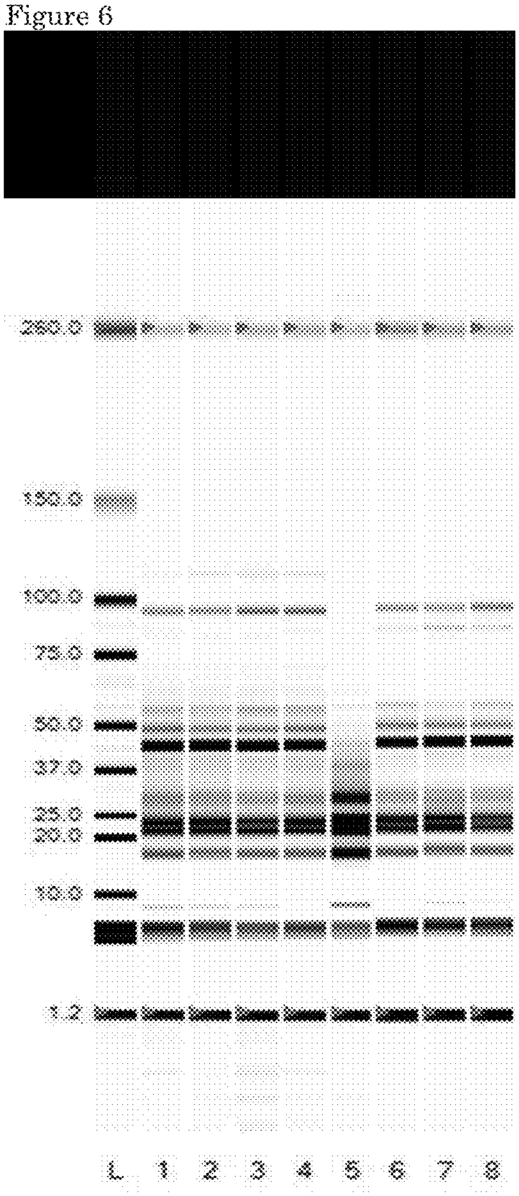
FIG. 6: total protein isolate comprising all protein fractions which are also present in the tuber (MF-PFJ). L protein standards, lane 1: Ex. 4 Exp. 9 MF-PFJ, lane 2: Ex. 4 Exp. 10 MF-PFJ, lane 3: Ex. 4 Exp. 11 MF-PFJ, lane 4: Ex. 5 MF-PFJ, lane 5: Ex. 5 End product (DF retentate), lane 6: Ex. 4 Exp. 9 End product (dry), lane 7: Ex. 4 Exp. 10 End product (dry), lane 8: Ex. 4 Exp. 11 End product (dry).

Experiments 8 and 9 show that diafiltration at a salt concentration of 0.5% NaCl and a ratio of protein solution to diafiltrate of 1:1 or 1:2 and 1:1 respectively can be used to obtain a potato protein isolate of good quality (84-86%). FIG. 6 shows that a total protein isolate is obtained comprising all protein fractions which are also present in the starting material.

In experiment 10 microfiltered and ultrafiltered PFJ was subjected to five separate diafiltration steps—two prior to TGA removal and three after TGA removal—using 0.5% KCl. These conditions result in a protein isolate of similar quality compared to when NaCl was used as salt during diafiltration. Also see FIG. 6.

Further, experiment 11 demonstrates that the quality of the native protein isolate can be significantly improved when using a UF and DF membrane with a MWCO of 50 kDa, instead of 5 kDa. Such conditions result in a protein isolate with 94% true protein content, compared to approximately 84% when a membrane having a MWCO of 5 kDa was used (See Experiments 8 and 9). FIG. 6 shows that a total protein isolate is obtained comprising all protein fractions which are also present in the starting material (MF-PFJ).

TABLE 3

| | | 8 | 9 | 10 | 11 |
|---|---|---|---|---|---|
| | | Pre-treatment | | | |
| | Unit | MF, UF | MF, UF, | MF, UF, DF, | MF, UF, |
| UF membrane | kDa | 5 | 5 | 5 | 50 |
| pH start-end | | 5.9-6.1 | 5.9-6.3 | 6.1-6.6 | 6.2-6.5 |
| Solids start-end | °Bx | 4.8-10.5 | 4.6-120.2 | 4.2-19 | 5.0-28.2 |
| σ start-end | $mS \cdot cm^{-1}$ | 12-13 | 12-13 | 12-16 | 12-10 |
| Dilution | | No | Yes | Yes | Yes |
| Solids | °Bx | | 12.9 | 12.4 | 10.9 |
| σ | $mS \cdot cm^{-1}$ | | 10 | 9 | 6 |
| Diafiltration | | | | | |
| DF Membrane | kDa | 5 | 5 | 5 | 50 |
| $V_{DF}$:$V_{PJ}$ | | 1:1 | 2:1, 1:1 | 1:1 | 1:1 |
| Nr of DF steps | | 5 | 2, 1 | 5 | 5 |
| DF Salt | | NaCl | NaCl | KCl | NaCl |
| DF [Salt] | (wt. %) | 0.5 | 0.5 | 0.5 | 0.5 |
| pH start-end | | 6.1-6.2 | 6.3-6.6 | 6.6-6.7 | 6.5-6.5 |
| Solids start-end | °Bx | 10.5-14.9 | 12.9-12.1 | 12.4-12.9 | 10.9-18.0 |
| σ start-end | $mS \cdot cm^{-1}$ | 13-9 | 13-9 | 9-10 | 8-7 |
| Drying | | spray | spray | spray | spray |
| Analysis | | | | | |
| TPC | % wt | 85.7 | 84 | 83 | 94 |
| MW < 35 kDa | % | | 56 | 58 | 54 |
| TNC | % wt | — | 86 | 84 | 94 |
| Total Sugars | % wt | <0.5 | <0.5 | <0.54 | <0.55 |
| TFAA | % wt | 0.83 | 0.56 | 0.05 | 0.98 |
| Sulfite | mg/kg | 7.4 | | | |
| TGA | mg/kg | 142.8 | 112 | 27 | 39 |
| Cadmium | mg/kg | 0.54 | 0.24 | 0.47 | 0.51 |
| Mercury | mg/kg | <0.025 | <0.01 | <0.01 | <0.01 |
| Lead | mg/kg | 0.2 | 0.28 | 0.20 | <0.1 |
| Arsenic | mg/kg | 0.04 | 0.07 | 0.06 | 0.06 |
| Phosphorous | mg/kg | — | 5761 | 5721 | 2797 |
| Sulfur | mg/kg | — | 14482 | 13269 | 13916 |
| Chlorine | mg/kg | — | 24524 | 15865 | 15245 |
| Potassium | mg/kg | — | 6025 | 55385 | 6014 |
| Calcium | mg/kg | — | 2061 | 1154 | 280 |
| Iron | mg/kg | — | 301 | 323 | 329 |
| Copper | mg/kg | — | 80 | 67 | 57 |
| Raw Ash | % wt | 6.5 | 8.2 | 9.3 | 4.2 |

TNC: Total nitrogen content;
TPC: True protein content;
TFAA: total free amino acids Example 5

Tuber processing water as obtained from potato tubers after starch and fiber removal (potato processing water) was used as raw material for production of a native potato protein protease inhibitor isolate at pilot scale. Potato processing water was subjected to a solids removal pre-treatment step of microfiltration using ceramic membranes with a pore size of 0.8 micrometres and operated at temperature around 23 f 2° C. and a constant flux of 100 l·(h·m$^2$)$^{-1}$. The microfiltered potato processing water (MF-PFJ) was stored in a tank to await further processing.

Microfiltered PFJ was subjected to ultrafiltration using a polyethersulphone membrane with a molecular weight cut-off (MWCO) of 5 kDa to obtain potato protein solution having a dissolved solids content of 19.2° Bx.

The pH of the ultrafiltered PFJ was subsequently set to 3.0 by dropwise addition of a 1 M HCl solution under stirring to form a slurry due to the precipitation of the patatin fraction of PFJ. The slurry was centrifuged at 4200 RPM for 10 minutes, and decanted. The supernatant was subjected to TGA removal using four columns packed hydrophobic resin at room temperature at a pH of around 3.5 and subsequently concentrated. The concentrate was diafiltered against a 6 kDa membrane using three times citrate buffer of pH 3.5, followed by three times 0.5% KCl solution (ratio concentrate to diafiltrate 5:3) to obtain a protein solution of 5.3° Bx and 90% protease inhibitor content (see also FIG. 6).

The results are summarized in table 4. It is shown that pH adjustment prior to diafiltration renders a protein isolate with good quality reflected in a true protein content of 81.4%. It is further demonstrated that this method allows to obtain a native potato protein isolate that is enriched in potato protease inhibitor fraction.

TABLE 4

| | Unit | 12<br>Pre-treatment<br>MF, UF, pH, Solids |
|---|---|---|
| UF membrane | kDa | 5 |
| pH start-end | | 6.0-3.1 |
| Solids start-end | °Bx | 4.8-8.3 |
| σ start-end | $mS \cdot cm^{-1}$ | 12-23 |
| Diafiltration | | |
| Membrane | kDa | 6 |
| $V_{DF}$:$V_{PJ}$ | | 3:5 |
| Salt | | KCl |
| [Salt] | (%) | 0.5 |
| pH start-end | | 3.1-3.7 |
| Solids start-end | | 8.3-5.3 |
| σ start-end | $mS \cdot cm^{-1}$ | 23-7 |
| Drying | | none |
| Analysis | | |
| True Protein Content | % wt | 81.4 |
| MW < 35 kDa | % | 90 |
| Total Nitrogen Content | % wt | 81.4 |
| TGA | mg/kg | 118 |
| Cadmium | mg/kg | <0.23 |
| Mercury | mg/kg | <0.23 |
| Lead | mg/kg | <2.3 |
| Arsenic | mg/kg | <1.2 |
| Phosphorous | mg/kg | 814 |
| Sulfur | mg/kg | 14535 |
| Chlorine | mg/kg | 43023 |
| Potassium | mg/kg | 52326 |
| Calcium | mg/kg | 1395 |
| Iron | mg/kg | 277 |
| Copper | mg/kg | 133 |
| Raw Ash | % wt | 9.3 |

Example 6

Microfiltered PFJ (300 L) was subjected to ultrafiltration having a kDa membrane to obtain a concentrated protein solution (35 L, 22.7° Bx). The concentrated protein solution was subjected to diafiltration by addition of 50 L of water (ratio concentrate to diafiltrate 7:10). The conductivity was decreased from 12 mS/cm (before addition of water) to 6.2 mS/cm (after addition of water). The diafiltered solution was concentrated again (35 L) and subjected to another 50 L of water, resulting in a further decrease of conductivity to 3.5 mS/cm. Upon addition of water, a white precipitate was formed and the solution turned from clear and orange to white and milky, indicating the precipitation of protein. NaCl (250 g) was added to obtain a clear, orange solution again, resulting in an increase of conductivity to 8 mS/cm.

Figure 3:
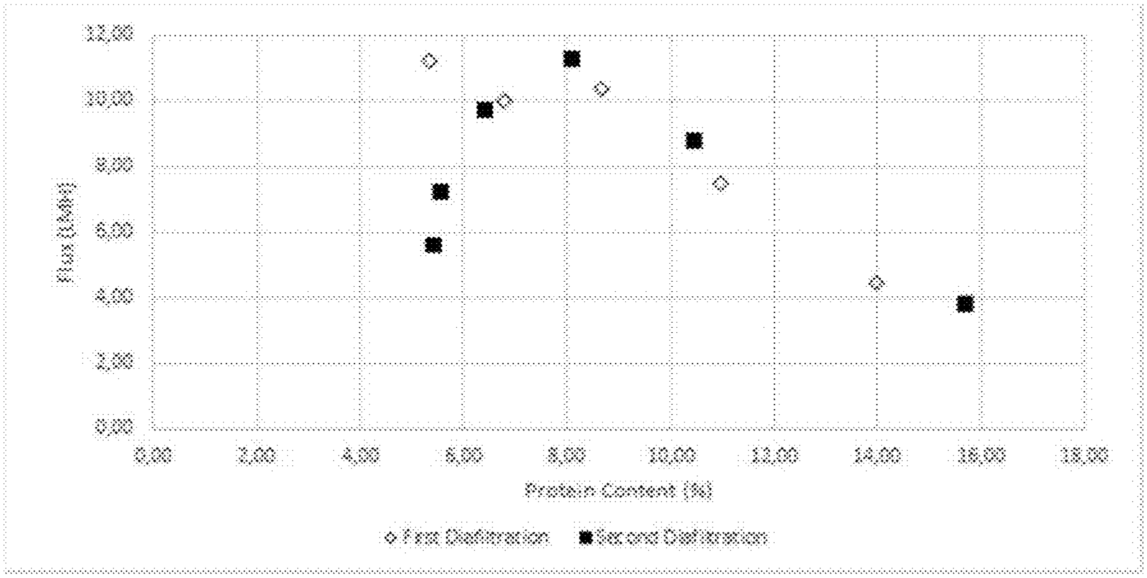
FIG. 3: flux-concentration plot during the first and second diafiltration of example 6.

A flux-concentration plot is shown in FIG. 3. From this plot it can be derived that the flux was reduced by 50% upon the addition of the second volume of water. This reduction in flux indicates clogging of the membrane. The flux was recovered upon the addition of NaCl, which indicates that the protein was solubilized again.

These results demonstrate that it is essential to maintain a conductivity of the protein solution above at least 5 mS/cm, preferably at least 8 mS/cm to avoid precipitation of protein, leading to both protein loss and membrane clogging and fouling. This can be achieved by monitoring the conductivity of the pretreated tuber processing water and/or by monitoring the conductivity of the salt solution.

Example 7

Tuber processing water as obtained from sweet potato and peeled cassava tubers after starch and fiber removal (sweet potato and cassava processing water) was used as raw material for production of a native total protein isolate. The processing water was subjected to a solids removal pretreatment step of ultrafiltration using an Amicon M-2000 ultrafiltration cell equipped with a 10 kDa MWCO membrane.

The ultrafiltered sweet potato juice was subsequently diafiltrated against a 10 kDa MWCO membrane using 0.5% NaCl solution (ratio concentrate to diafiltrate 1:5). The concentrate was subjected to two more diafiltration steps using 0.5% NaCl solution (ratio concentrate to diafiltrate 1:2 and 1:1) to obtain a protein solution.

The ultrafiltered peeled cassava juice was subjected to diafiltration against a 10 kDa MWCO membrane using 0.5% NaCl solution (ratio concentrate to diafiltrate 1:1.5) to obtain a protein solution.

The chemical composition of the treated tuber juices are shown in table and compared to untreated juice.

| — | — | Raw Sweet Potato Juice | Diafiltration concentrate | Raw Cassave Juice | Diafiltration concentrate |
|---|---|---|---|---|---|
| Sugars | g/kg DM | 122 | 30 | 767 | 388 |
| Minerals | g/kg DM | 35 | 111 | 278 | 136 |
| Ash | g/kg DM | nm | 146 | nm | 167 |
| Potassium | g/kg DM | 23 | nd | 218 | 75 |
| Chlorine | g/kg DM | 6 | 86 | 6 | 33 |
| Kjeldahl N*6.25 | g/kg DM | 85 | 669 | 307 | 241 |
| Free Amino Acids | g/kg DM | 12 | nd | 87 | 9 |
| True Protein | g/kg DM | 35 | 551 | 119 | 178 |

nd: not detected

The results show that the method is successful in providing a native tuber juice having a high native protein content. In both cases a significant increase in true protein content was observed, whilst the presence of contaminants such as sugar and free amino acids was substantially decreased.

Example 8

To test the solubility of protein at native pH (6-6.3) and at various conductivities, a total potato protein comprising protease inhibitor and patatin was used. The potato protein was obtained by microfiltration of potato juice, ultrafiltration to 10% of the original volume, and diafiltration using the protocol of Example 4, experiment 8 without spray drying and using pure water until the conductivity of the retentate was at 8 mS/cm.

The resulting aqueous potato protein was diluted in aqueous solutions of NaCl at conductivities 3.7, 5.3, 6.7, 9.2, and 14 mS/cm to obtain solutions with a protein concentration of 1.3% wt. Additionally, a dilution with pure water was made yielding a potato protein solution at a conductivity of 1.3 mS/cm and a protein concentration of 1.3% wt.

Figure 4:
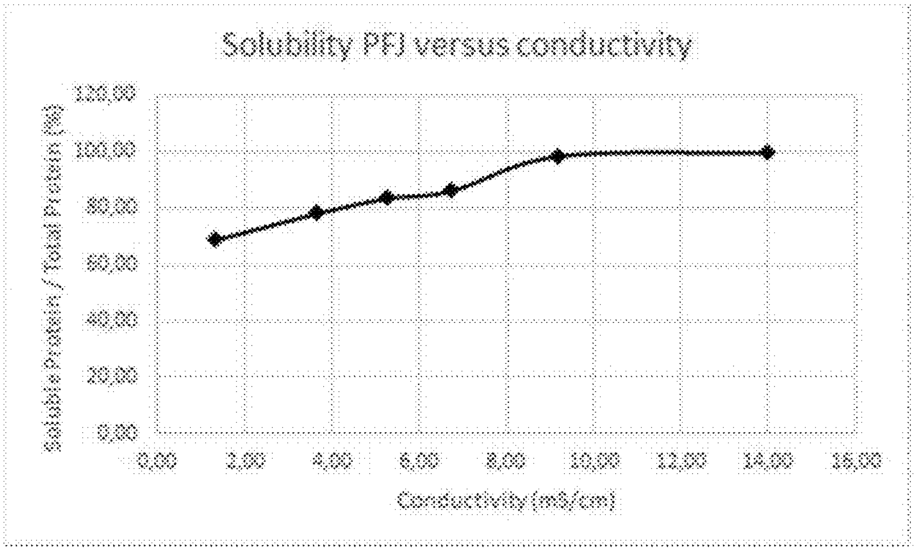
FIG. 4: solubility of potato total isolate at various conductivities

Subsequently, the solutions were left to stir for 1 hour before centrifugation. The protein concentration in the supernatant was determined by sprint and compared to the original protein concentrate. The result are shown in FIG. 4.

This experiment shows that protein precipitation in an aqueous mixture comprising protease inhibitor and patatin is unacceptable if the conductivity falls below 5 mS/cm. The conductivity during diafiltration must be maintained above 5 mS/cm, and more preferably above 8 mS/cm at all times.

Example 9

The protein isolate described in Example 8 was subjected to diafiltration using a solution against NaCl solutions having conductivities of 1.34, 3.65, 4.72, 5.25, 6.72, 8.72, 9.2, 12, 14 and 49.5 mS/cm.

Figure 5:
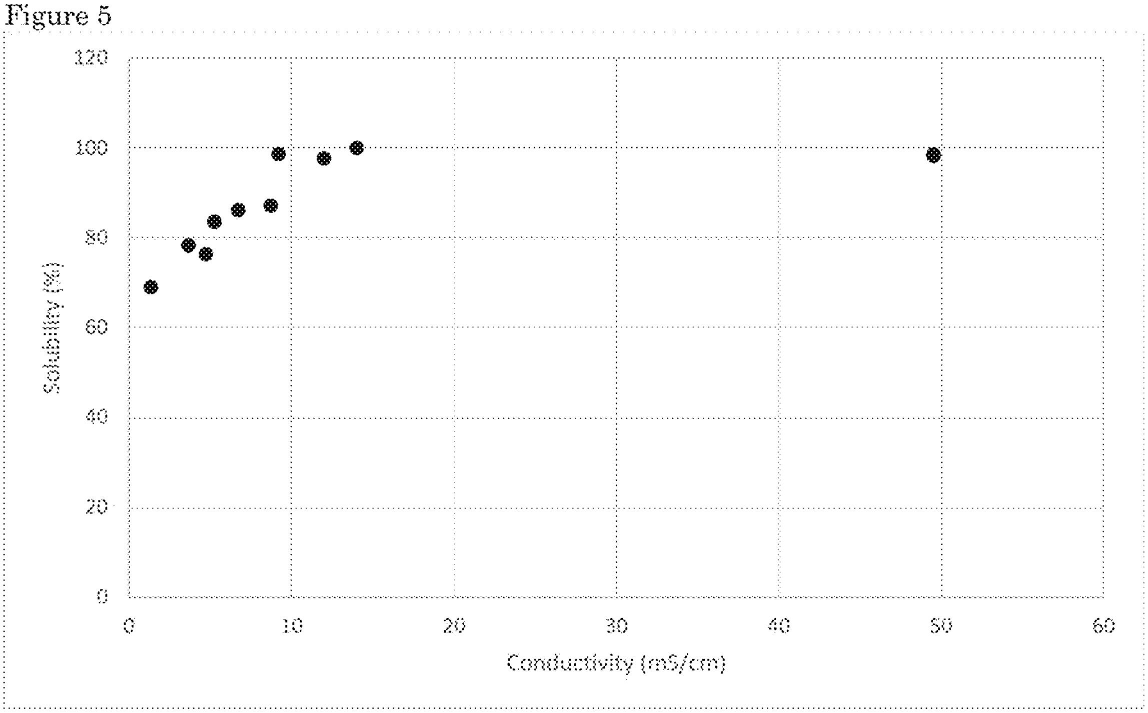
FIG. 5: solubility of potato total isolate at various conductivities

The results are displayed in FIG. 5. Diafiltration against a salt solution having a conductivity of less than 5 mS/cm results in an unacceptable precipitation. Increasing the conductivity to above 5 mS/cm, preferably above 8 mS/cm allows for convenient protein isolation, which results in improved protein products.

The invention claimed is:

1. A method for isolating a native tuber protein isolate comprising a) processing at least one tuber to obtain tuber processing water comprising native tuber protein;

b) subjecting said tuber processing water to a pretreatment comprising:

solids removal by microfiltration and concentration by ultrafiltration, which pretreatment results in a pretreated tuber processing water having a conductivity of 2-20 $mS\cdot cm^{-1}$ comprising native tuber protein;

c) a step of diafiltration of the pretreated tuber processing water against a salt solution having a conductivity of at least 5 $mS\cdot cm^{-1}$ using a 3-500 kDa membrane, thereby obtaining said native tuber protein isolate as the diafiltration retentate, said native tuber protein isolate comprising, relative to dry matter, at most 1.0 wt % of a total of glucose, fructose and glucose, and at most 1.0 wt % of tuber free amino acids, wherein the native tuber protein isolate has a protein content of at least 85% relative to dry matter and a solubility of at least 85%.

2. A method according to claim 1, wherein the native tuber protein isolate is a total native tuber protein isolate, defined as an isolate comprising all tuber protein in native form.

3. A method according to claim 1, wherein the method further comprises a step of glycoalkaloid removal, to obtain a tuber protein isolate comprising at most 200 mg/kg glycoalkaloids.

4. A method according to claim 3, wherein the glycoalkaloid removal step is performed as part of step b, or after step c.

5. A method according to claim 1, wherein said processing to obtain tuber processing water comprises pulping, mashing, rasping, grinding, pressing or cutting of the tuber.

6. A method according to claim 5, wherein said processing further comprises a step of starch removal.

7. A method according to claim 1, wherein said at least one tuber is peeled prior to processing.

8. A method according to claim 1, wherein diafiltration is performed using membranes having a molecular weight cutoff of 5-300 kDa.

9. A method according to claim 1, wherein the diafiltration is performed against a salt solution comprising chloride.

10. A method according to claim 1, wherein the conductivity of the salt solution is 5-20 $mS\cdot cm^{-1}$.

11. A method according to claim 1, wherein the pH during diafiltration is lower than 4.0, or higher than 5.5.

12. A method according to claim 1, wherein the diafiltration retentate is subjected to a step of ultrafiltration to obtain a concentrated tuber protein isolate.

13. A method according to claim 1, wherein the ultrafiltration step is performed using an ultrafiltration membrane having a MWCO of 5-200 kDa.

14. A method according to claim 1, wherein the first of diafiltration or ultrafiltration provides a permeate comprising tuber free amino acids.

15. A method according to claim 14, wherein the permeate is subsequently dried to result in a tuber free amino acid composition.

16. A method according to claim 15, wherein the permeate is concentrated by ultrafiltration, reverse osmosis and/or freeze concentration prior to drying.

17. A method according to claim 1, wherein the pH of the tuber protein isolate is adjusted to higher than 2.5.

18. A method according to claim 1, wherein the pH of the tuber protein isolate is adjusted to lower than 3.5.

19. A method according to claim 1, wherein the tuber protein isolate is subsequently dried to obtain a native tuber protein powder.

20. A method according to claim 19, wherein prior to drying, the tuber protein isolate is subjected to a further concentration step.

21. A method according to claim 19, wherein prior to drying, the tuber protein isolate is adjusted to a pH of 5.5-7.0.

22. A method according to claim 19, wherein said drying is performed by freeze drying or spray spraying.

23. A method according to claim 1, wherein the diafiltration retentate comprises as a percentage of dry matter at least 75 wt. % native tuber protein, at most 1.0 wt. % the total of glucose, fructose and sucrose, at most 1 wt. % tuber free amino acids, at most 10 mg/kg sulfite, at most 200 mg/kg glycoalkaloids, and/or at most 5 mg/kg heavy metals selected from the group consisting of cadmium, mercury, lead and arsenic.

24. A method according to claim 1, wherein the method is operated to result in at least 5 kg of protein per hour.

25. A method according to claim 1, wherein the native tuber protein isolate comprises native protease inhibitor and native patatin.

26. A method according to claim 1, wherein the obtained native tuber protein isolate comprises, as a percentage of dry matter, at most 0.5 wt % of the total of glucose, fructose and glucose, and at most 0.5 wt % of the tuber free amino acids.

* * * * *